United States Patent
Lego et al.

(10) Patent No.: US 11,340,202 B2
(45) Date of Patent: May 24, 2022

(54) CALIBRATING AN OXYGEN SENSOR OF A DOMESTIC APPLIANCE

(71) Applicant: BSH Hausgeräte GmbH, Munich (DE)

(72) Inventors: Dieter Lego, Karlsruhe (DE); Hans-Jürgen Bauer, Traunstein (DE)

(73) Assignee: BSH Hausgeräte GmbH, Munich (DE)

( * ) Notice: Subject to any disclaimer, the term of this patent is extended or adjusted under 35 U.S.C. 154(b) by 399 days.

(21) Appl. No.: 16/335,273

(22) PCT Filed: Nov. 2, 2017

(86) PCT No.: PCT/EP2017/077995
§ 371 (c)(1),
(2) Date: Mar. 21, 2019

(87) PCT Pub. No.: WO2018/083139
PCT Pub. Date: May 11, 2018

(65) Prior Publication Data
US 2020/0018721 A1    Jan. 16, 2020

(30) Foreign Application Priority Data
Nov. 2, 2016  (DE) .......................... 102016221446.2

(51) Int. Cl.
*G01N 33/00*  (2006.01)
*F24C 7/08*  (2006.01)
(Continued)

(52) U.S. Cl.
CPC ........... *G01N 33/0006* (2013.01); *F24C 7/08* (2013.01); *F24C 15/003* (2013.01); *G01L 27/00* (2013.01);
(Continued)

(58) Field of Classification Search
CPC .. G01N 33/0006; G01N 27/00; G01N 27/407; G01N 27/4175
See application file for complete search history.

(56) References Cited

U.S. PATENT DOCUMENTS 4,475,823 A * 10/1984 Stone ................... G01K 15/005
374/1
4,489,590 A * 12/1984 Hadden .............. G01N 33/0006
73/1.04
(Continued)

FOREIGN PATENT DOCUMENTS

AT    398483 B * 12/1994  ............. F24B 1/028
CN    103314287 A    9/2013
(Continued)

OTHER PUBLICATIONS

ESPACENET Machine Translation of DE 102010054607 B3 Which Originally Published on Jan. 12, 2012. (Year: 2012).*
(Continued)

*Primary Examiner* — David A. Rogers
(74) *Attorney, Agent, or Firm* — Michael E. Tschupp; Andre Pallapies; Brandon G. Braun

(57) ABSTRACT

A method for calibrating an oxygen sensor of a household appliance includes a calibration process which is automatically started when at least one status parameter of the household appliance has at least reached a predetermined threshold value. The household appliance can be a steam cooking appliance, and the oxygen sensor can be a lambda probe.

19 Claims, 1 Drawing Sheet

(51) Int. Cl.
*F24C 15/00* (2006.01)
*G01N 27/407* (2006.01)
*G01N 27/417* (2006.01)
*G01L 27/00* (2006.01)
*A47J 27/04* (2006.01)

(52) U.S. Cl.
CPC ....... *G01N 27/407* (2013.01); *G01N 27/4175* (2013.01); *A47J 27/04* (2013.01); *A47J 2027/043* (2013.01)

(56) References Cited

U.S. PATENT DOCUMENTS

| | | | | |
|---|---|---|---|---|
| 4,914,424 A * | 4/1990 | Hirao | ................. | G01N 27/4065 340/632 |
| 5,402,665 A * | 4/1995 | Hart | ................. | G01D 18/008 340/632 |
| 5,457,963 A * | 10/1995 | Cahill-O'Brien | ...... | G05D 21/02 62/78 |
| 6,227,033 B1 | 5/2001 | Kainz | ................. | F02D 41/123 123/674 |
| 6,244,093 B1 * | 6/2001 | Parekh | ................. | G01N 33/0006 73/1.06 |
| 6,711,425 B1 * | 3/2004 | Reuss | ................. | A61B 5/14542 600/323 |
| 7,558,690 B2 | 7/2009 | Curtius et al. | | |
| 8,019,544 B2 * | 9/2011 | Needelman | ............ | B64G 1/361 701/513 |
| 8,887,724 B2 * | 11/2014 | Feng | ................. | A61M 16/01 128/205.24 |
| 9,423,377 B2 * | 8/2016 | Roelver | ............ | G01N 27/4077 |
| 9,632,981 B2 * | 4/2017 | Chan | ................. | G04F 13/04 |
| 9,804,137 B2 | 10/2017 | Doering | | |
| 10,228,145 B2 * | 3/2019 | Erbe | ................. | F24C 7/081 |
| 10,386,345 B2 * | 8/2019 | Hakeem | ................. | G01N 33/2829 |
| 11,078,859 B2 * | 8/2021 | Saleem | ................ | F02D 41/1494 |
| 11,079,364 B2 * | 8/2021 | Leger | .................... | G04G 21/02 |
| 2004/0139732 A1 * | 7/2004 | Wang | ................. | F02D 41/1441 60/277 |
| 2007/0217952 A1 * | 9/2007 | Kruempelmann | .. | F24C 15/2014 422/78 |
| 2008/0050481 A1 * | 2/2008 | Morris | ................. | A23L 3/3418 426/232 |
| 2011/0048100 A1 * | 3/2011 | McEwen | ................ | G08B 29/20 73/1.06 |
| 2012/0085435 A1 * | 4/2012 | Feng | ...................... | A61M 16/20 137/467.5 |
| 2016/0116171 A1 | 4/2016 | Boedicker | | |
| 2017/0086258 A1 | 3/2017 | Bodechtel et al. | | |
| 2021/0114109 A1 * | 4/2021 | Pauzon | ................... | B22F 12/41 |

FOREIGN PATENT DOCUMENTS

| | | | | |
|---|---|---|---|---|
| DE | 102010054607 B3 | | 1/2012 | |
| DE | 102012201471 A1 | | 8/2013 | |
| EP | 2741012 A1 | | 6/2014 | |
| EP | 2615375 B1 * | | 10/2016 | ............. F24C 7/085 |
| GN | 102132106 A | | 7/2011 | |
| JP | H051822 A | | 1/1993 | |
| JP | H06242057 A * | | 9/1994 | |
| JP | H09143565 A | | 6/1997 | |
| JP | 5668611 B2 * | | 2/2015 | ......... F02D 41/2474 |
| WO | 2014001097 A1 | | 1/2014 | |

OTHER PUBLICATIONS

National Search Report CN 201780068276.5 dated May 18, 2021.
National Search Report CN 201780068276.5 dated Nov. 4, 2020.
International Search Report PCT/EP2017/077995 dated Jan. 26, 2018.

* cited by examiner

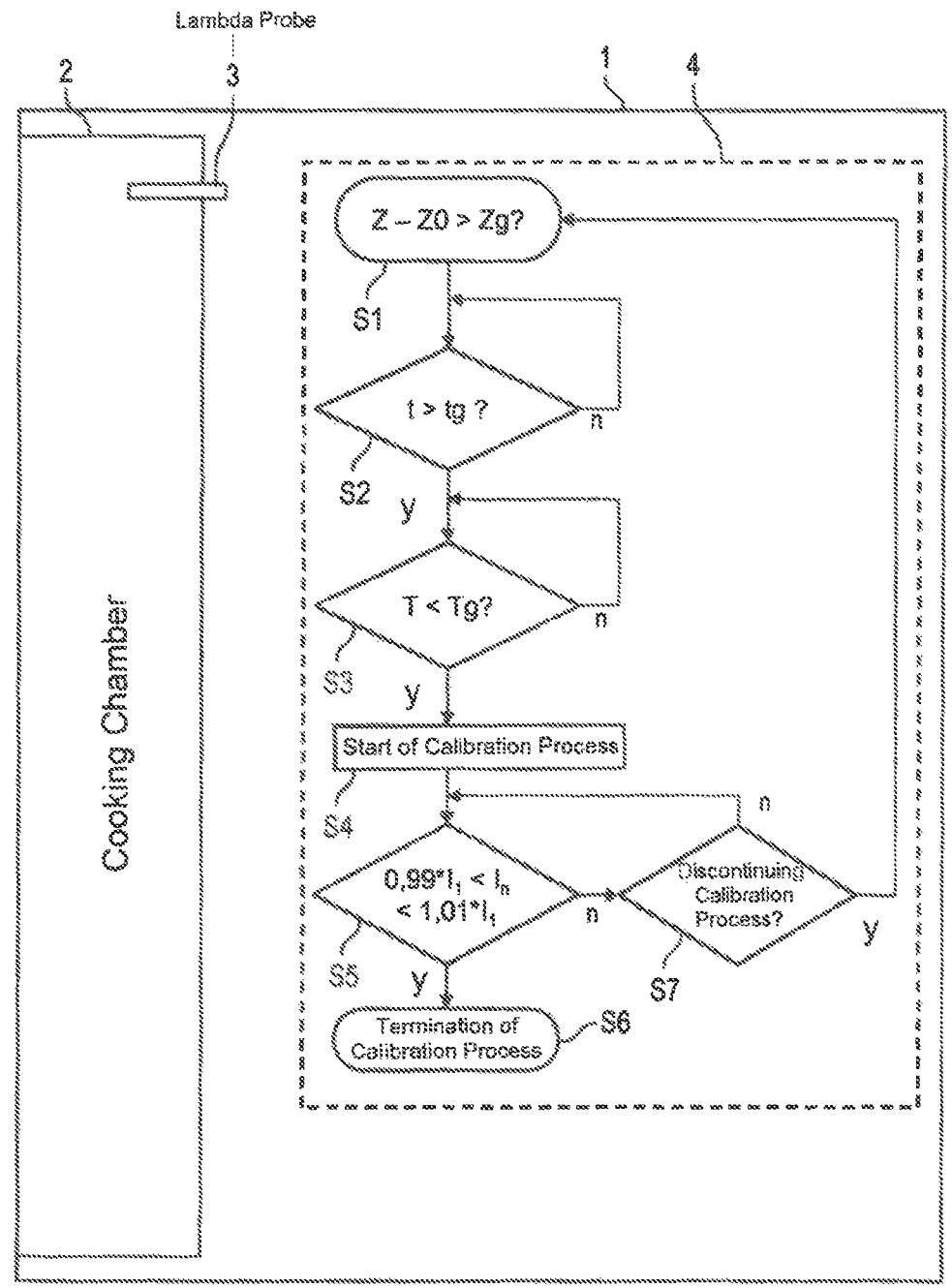

CALIBRATING AN OXYGEN SENSOR OF A DOMESTIC APPLIANCE

CROSS-REFERENCES TO RELATED APPLICATIONS

This application is the U.S. National Stage of International Application No. PCT/EP2017/077995, filed Nov. 2, 2017, which designated the United States and has been published as International Publication No. WO 2018/083139 A1 and which claims the priority of German Patent Application, Serial No. 10 2016 221 446.2, filed Nov. 2, 2017, pursuant to 35 U.S.C. 119(a)-(d).

BACKGROUND OF THE INVENTION

The invention relates to a method for calibrating an oxygen sensor of a household appliance. The invention is advantageously applicable, in particular, to steam cooking appliances, for example ovens having a steam cooking function or stand-alone steam cookers.

DE 10 2010 054 607 B3 relates to a method for operating a cooking appliance having the following steps: detecting the oxygen partial pressure via a lambda probe, determining the actual ambient pressure based on the detected oxygen partial pressure and calibrating the cooking appliance based on the actual ambient pressure. "Calibrating" is understood here as identifying the actual ambient pressure of the cooking appliance and adapting operating processes to the actual ambient pressure. In this case, it is a prerequisite that the oxygen partial pressure determined by means of the lambda probe is able to be correctly correlated with the air pressure. In order to reduce the influence of the air humidity on the measurement of the oxygen partial pressure, the "calibration" may be executed at predetermined times of day. Not disclosed is a calibration of the lambda probe in order to take into account drift of the lambda probe.

DE 10 2012 021 928 A1 relates to a method and a device for the calibration of an exhaust gas sensor which is arranged in a measurement chamber, wherein the measurement chamber is provided in or adjacent to an exhaust gas channel of an internal combustion engine. At the start of a calibration phase, exhaust gas located in the measurement chamber is displaced by filling the measurement chamber with calibration gas and when the calibration phase is terminated exhaust gas is introduced into the measurement chamber and/or the exhaust gas is diffused there.

EP 2 161 569 A2 relates to a method for calibrating a measurement signal provided by a sensor arranged in an exhaust gas line of an internal combustion engine, in particular a NOx sensor and/or a lambda sensor, wherein the measurement signal detected by a measurement tip of the sensor is able to be represented in a characteristic curve as a function of the NOx concentration, and wherein the characteristic curve has a zero point deviation which is to be balanced in a continuous or discontinuous manner. A method for calibrating a sensor is specified which is able to be executed independently of an overrun mode of the internal combustion engine. This is achieved in normal operation of the internal combustion engine by the balancing taking place by purge air flowing past the measurement tip of the sensor. To this end the measurement tip is either masked from the exhaust air line or purge air is blown in a targeted manner onto the measurement tip.

BRIEF SUMMARY OF THE INVENTION

It is the object of the present invention to overcome at least partially the drawbacks of the prior art and, in particular, to provide a possibility of identifying and compensating for drift of an oxygen sensor of a household appliance in a reliable manner.

This object is achieved according to the features of the independent claims. Preferred embodiments are able to be derived, in particular, from the dependent claims.

The object is achieved by a method for calibrating an oxygen sensor of a household appliance, in which a calibration process is started when at least one status parameter of the household appliance has at least reached a predetermined threshold value.

This method is based on the recognition that in the course of the service life of the oxygen sensor the measured values thereof drift so that the absolute accuracy of the measured values is continuously impaired. This drift which is typically noticeable after weeks or months differs from one oxygen sensor to another and also as a function of the application of harmful substances, such as for example silicone.

This method has the advantage that the drift may be reliably identified and optionally compensated. In turn, a greater absolute measurement accuracy of the oxygen sensor may be achieved thereby. Since an oxygen concentration in a treatment chamber of the household appliance is inversely proportional to the level of moisture in the treatment chamber, the oxygen concentration measured by the oxygen sensor may thus be used as a measurement of the moisture content in the treatment chamber.

This is advantageous, in particular, if the oxygen sensor is used for regulating the moisture of the cooking chamber. Since when using the moisture content as a guide variable (setpoint value) for regulating the moisture, the absolute measured values are important and the drift of the measured values has a direct influence on the regulating accuracy. A calibration according to the described method increases the measurement accuracy and thus the regulating accuracy.

As a further advantage the calibration may be executed by simple appliance-specific means. No additional components or test gases are necessary. Also no information about external environmental parameters is required, such as the geodesic level of the point of installation or a time of day at the point of installation.

The oxygen sensor may protrude into the cooking chamber or may be connected by gas technology to the cooking chamber.

The calibration of the measured values comprises taking into account and optionally correcting a drift of the measured values of the oxygen sensor. The drift, in particular, comprises a chronological alteration of the measured values in a constant measuring environment. Thus for the same oxygen partial pressure or oxygen concentration the measured values may migrate with time. By means of the calibration a defined relationship between the oxygen partial pressure and the measured values may be restored. For example, a measured value may be assigned to a previously known oxygen partial pressure or oxygen concentration, whereby this measured value may serve as a new reference.

"Status parameter of the household appliance" is understood, in particular, as a status parameter which is assigned to the household appliance as such and not only an environmental parameter such as a time of day or point of installation of the household appliance. By the dependence of the start of the calibration process on the at least one status parameter, advantageously a plausibility check is made to establish whether a measuring environment which is suitable for the calibration process is present. The suitable measuring environment, in particular, is a measuring environment with a sufficiently known oxygen concentration. The status parameter and/or the threshold values thereof thus link the calibration process to conditions which ensure a known oxygen value with sufficient accuracy. In particular, the oxygen concentration of atmospheric air with an oxygen component of 20.95% is used as the known oxygen concentration.

A status parameter at least reaching a predetermined threshold value may encompass the predetermined threshold value being exactly reached, or alternatively or additionally the predetermined threshold value being exceeded or fallen below. For example, a status parameter may have at least reached a predetermined threshold value when the value of the status parameter is equal to ("="), greater than or equal to (">=") or greater than (">") the predetermined threshold value.

It is a development that the oxygen sensor is also used in order to control cooking processes based on a change to the moisture content during the cooking process. For example, a maximum level of moisture in the cooking chamber may be identified in this manner and used for establishing a degree of readiness of the cooked food. By such a use of the oxygen sensor, the drift of the measured values does not constitute a practical problem since a response is only made to changes to the measured values and the absolute measured values are not evaluated.

The oxygen sensor may be calibrated for the first time, for example, before or during set-up (first calibration). The described method may thus be regarded as a recalibration.

It is a development that the method is executed automatically by the household appliance, i.e. without the intervention of a user. This permits a particularly high level of user-friendliness since no specific handling is required by the user for the calibration process. Instead, the calibration process may run unnoticed in the background. In particular, the method may be executed only automatically. Alternatively or additionally, it is possible that the household appliance prompts the user to execute a calibration process and to this end, for example, to open the cooking chamber door for a displayed time period when the cooking chamber is cool. Such an intervention of a user, for example, may be provided if it had not been possible for the household appliance to execute a calibration process successfully within a predetermined time period (for example a predetermined operating time period since the last calibration, for example of 100 hours) since the status conditions had not been fulfilled.

It is a development that the household appliance is a kitchen appliance, in particular a cooking appliance.

It is an embodiment that the household appliance is a steam cooking appliance. The method is also able to be used particularly advantageously since an accurate regulation of the moisture may significantly improve a cooking result. The steam cooking appliance has a cooking chamber as the treatment chamber, to which steam is able to be applied. The steam cooking appliance may be a stand-alone steam cooking appliance. Alternatively, it may be a cooking appliance with a steam treatment function, for example, an oven with an additional steam cooking function ("added steam"). The cooking chamber may have a steam generator for the application of steam, for example a steam generator arranged outside the cooking chamber (boiler, instant water heater, etc.) or a heatable water tray located in the cooking chamber.

The household appliance, however, may also be a dishwasher with a washing chamber as the treatment chamber, a laundry dryer with a laundry drum housing as the treatment chamber, etc.

It is an embodiment that a lambda probe is used as the oxygen sensor. A lambda probe (also denoted a lambda sensor) has the advantage that it is particularly robust, in particular even relative to high temperatures, and reliable.

It is a further embodiment that the calibration process is automatically started when a plurality of status parameters of the household appliance have reached a respective predetermined threshold value. This increases the reliability of the calibration process, since now a plausibility check may be made by repeated inquiries of variable content to establish whether a measuring environment which is suitable for the calibration process is present. In particular, the plurality of status parameters have reached their respective predetermined threshold value at the same time or within a predetermined time interval. The predetermined time interval, for example, may be the time period which is required in order to make an inquiry relative to the plurality of status parameters.

It is a further embodiment that the at least one status parameter of the household appliance comprises a time period which has elapsed since the last calibration process and the calibration process is automatically started when this time period has reached or exceeded an associated threshold value. The advantage of this embodiment is that the method is not executed more frequently than is necessary.

It is a development that the time period is an operating period which permits particularly long intervals between the calibration processes. The operating period may be undertaken by means of an operating time hour meter which is advantageously already present in many household appliances. The threshold value serving as minimum operating period may be multiples of 10 hours, for example 30 hours.

It is a further embodiment that the at least one status parameter of the household appliance comprises a door opening time and the calibration process is automatically started when the door opening time has reached or exceeded an associated threshold value. This provides the advantage that the oxygen sensor is in fresh ambient air during the calibration process, since the ambient air may penetrate into the cooking chamber through the loading opening and displace air present there, and optionally other gases and moisture. The door opening time corresponds to the time when the cooking chamber door is continuously opened. An open status of the cooking chamber door may be established, for example, by means of a door opening switch. The threshold value of the door opening time corresponds, in particular, to a minimum time which a cooking chamber door should be open in order to reach a sufficiently thorough air exchange. The door opening time may, for example, be 10, 20, 30 or 60 seconds.

It is a development that the door opening time is zero when the cooking chamber door is closed so that a positive inquiry relative to the door opening time comprises the door to the cooking chamber being open for starting the calibration process.

It is a further embodiment that the at least one status parameter of the steam cooking appliance comprises a temperature in the treatment chamber (for example a cooking chamber temperature) and the calibration process is automatically started when this temperature has reached or fallen below an associated threshold value (limit temperature). As a result, it is advantageously achieved that typically the air exchange with the oven environment is substantially terminated and thus generally no moisture is discharged from the cooked food. The limit temperature may, for example, be between 45° C. and 60° C., in particular approx. 50° C.

It is a development that the calibration process is automatically started when the time period has reached or exceeded its threshold value since the last calibration process, the door opening time has reached or exceeded its threshold value and the cooking chamber temperature has reached or fallen below its threshold value.

It is a further embodiment that during the calibration process a pump flow of a lambda probe serving as an oxygen sensor is measured and when the pump flow remains for a predetermined time period within a predetermined value range or value margin ("fluctuation margin") a value of the pump flow is selected from this fluctuation margin as a reference value of the pump flow. As a result, in a simple and reliable manner a new reference value of the pump flow may be determined and may be used for the operation of the cooking appliance, in particular for measuring the level of moisture. This new reference value is adapted to the air present on the oxygen sensor during the calibration process. This embodiment is also applicable to other types of oxygen sensors with corresponding measured values.

The purpose of the predetermined time period is that measured values also reliably fall within the fluctuation margin in a chronological manner. The predetermined time period may, for example, be at least 30 seconds.

It is a further embodiment that an average value of the fluctuation margin is selected as the calibrated reference value of the pump flow. The average value of the fluctuation margin may, in particular, be calculated as an average value from a minimum value and a maximum value of the fluctuation margin. The fluctuation margin may, for example, be +/−1%, +/−2%, etc.

It is a development that for executing the calibration a measured value Im of the pump flow is determined and it is monitored whether further measured values Ip detected in the predetermined time period remain within the fluctuation margin. The upper limit and the lower limit of the fluctuation margin may be determined in a fluctuation range of +/−m % by 0.99·Im and/or 1.01·Im. In this case, in a development all further measured values Ip remain within the fluctuation margin, i.e. for example whether 0.99·Im<Ip<1.01 Im applies. If this is the case, for example, the measured value Im may be used as a new reference value, in particular as the measured value corresponding to an oxygen component of 20.95%. If this is not the case, the calibration process may be discontinued or repeated. The measured value Im may, for example, be a first measured value.

It is a further embodiment that the calibration process is discontinued if it lasts longer than a predetermined threshold value, for example longer than two minutes. Thus a "suspension" of the calibration process may be prevented in the case of calibration tests being repeatedly executed unsuccessfully.

It is a further embodiment that the calibration process is discontinued if the cooking chamber door is closed. This further increases the reliability of the calibration process.

It is a further embodiment that the results of the calibration processes are stored and evaluated for a malfunction of the oxygen sensor. This advantageously permits a timely identification of a possible malfunction of the oxygen sensor. The result of the calibration process may be a new result value. The evaluation may, for example, comprise a comparison of the new and/or current result value with at least one previously determined (historical) result value. For example, a malfunction may be established if the current result value deviates by more than one predetermined difference from the previously valid result value or from an average value of a set of stored result values. Moreover, for example, a malfunction may be established if a current result value deviates from a historical trend of result values, for example does not drop as before, but rises, etc.

It is a further embodiment that the reference values of the pump flow of a lambda probe are used as results.

The object is also achieved by a household appliance comprising a treatment chamber, an oxygen sensor and a data processing device for determining a moisture content in the treatment chamber based on measured values of the oxygen sensor, wherein the household appliance is designed for calibrating the measured values according to the above-described method. The household appliance may be configured in a similar manner to the method and has the same advantages.

It is an embodiment that the household appliance is a steam cooking appliance which has a cooking chamber as the treatment chamber, to which steam is able to be applied.

It is a development that the data processing device is designed to execute the method. The data processing device may also be designed to control further functions of the household appliance, for example cooking programs or other programs such as cleaning programs, etc. The data processing device may be a control device of the household appliance.

It is a further development that the data processing device comprises a memory device or is coupled to a memory device in which results from calibration processes (results history) may be stored. The memory device may, in particular, be a EEPROM memory device or other non-volatile, in particular erasable, memory device.

BRIEF DESCRIPTION OF THE DRAWINGS

The above-described properties, features and advantages of this invention and the manner in which they are achieved will become more clear and more easily comprehensible in connection with the following schematic description of an exemplary embodiment which is described in more detail in connection with the drawings.

FIG. 1 to this end shows a possible flow diagram of a method for calibrating measured values of an oxygen sensor of a steam cooking appliance.

DETAILED DESCRIPTION OF EXEMPLARY EMBODIMENTS OF THE PRESENT INVENTION

The household appliance in the form of a steam cooking appliance 1 comprises a cooking chamber 2 to which steam is able to be applied, an oxygen sensor in the form of a lambda probe 3 and a data processing device 4. The data processing device 4 is designed to determine a moisture content in the cooking chamber 2 based on measured values of the lambda probe 3. The data processing device 4 is further designed to execute the method. The data processing device 4 may be a central control device for operating the steam cooking device 1.

In the method, the data processing device 4 monitors in a first step S1 whether a status parameter in the form of a time period Z-Z0 since the time Z0 of a last calibration is greater than a threshold value in the form of a predetermined time period Zg. In other words, in step S1 it is monitored whether from the last calibration executed at the time Z0 to the current time Z, the time period Zg has already elapsed. Zg may, for example, be 30 hours. If this is not the case, step S1 is repeated at a later time. Step S1 may be executed regularly by the data processing device 4. If this is the case, however, step S2 is executed. The times Z and Z0 and/or the time period Zg may, for example, be detected by means of an operating time hour meter of the steam cooking appliance 1.

In step S2 it is monitored whether a door opening time t of a cooking chamber door has exceeded a threshold value in the form of a predetermined time period tg, in this case for example a time period tg of 60 seconds. If this is not the case ("n"), step S2 is repeated. If, however, this is the case ("y"), step S3 is executed.

In step S3 it is monitored whether a cooking chamber temperature T has fallen below a threshold value in the form of a predetermined limit temperature Tg, here for example a limit temperature Tg of 50° C. If this is not the case ("n") step S3 is repeated. Alternatively, for example, it is possible to return to step S2. However, if this is the case ("y") step S4 is executed.

By the three steps S1 to S3, the probability is very high that the lambda probe 3 is surrounded by fresh ambient air with an oxygen component of approx. 20.95%.

In step S4—since all three conditions inquired in steps S1 to S3 are present—the calibration process is automatically started by the data processing device 4. To this end, in step S4, the lambda probe 3 is initially prepared for recording measurements, for example heated up.

In step S5, a pump flow I of the lambda probe 3 is then measured. Namely, initially a first measured value $I_1$ is recorded. In the following measurements which, for example, are carried out at intervals of five seconds, the associated measured values $I_n$ are examined by the data processing device 4 as to whether they are all within a fluctuation margin around the first measured value $I_1$, by way of example of $I_1+/-1\%$. The step S5 may be executed for a predetermined time period, for example for 30 seconds.

If step S5 is successful ("y"), in a following step S6 the first measured value $I_1$ is regarded as a new reference value of the pump flow I for an oxygen concentration of 20.95%. The calibration process is thus terminated.

If step S5 is unsuccessful ("n"), as a result in a step S7 an inquiry may be made as to whether the calibration process is to be discontinued. If this is the case ("y"), it is possible to proceed to the monitoring of step S1. If not ("n"), it is possible—optionally repeatedly—to return to step S5. For example, a predetermined number (for example a maximum of four times) of calibrating attempts according to step S5 may be executed and/or attempted, to complete step S5 successfully within a specified time period (for example with a threshold value of two minutes) before proceeding to step S7.

The inquiry in step S7 may also relate to whether, before successful execution, the cooking chamber door has been closed again.

The data processing device 4 may also be designed to store the reference values and thus to compile a history of these reference values. The data processing device 4 may also be designed to use the reference values—for example by a comparison of at least one previously determined reference value with the currently measured reference value—to evaluate a malfunction of the oxygen sensor.

Naturally the present invention is not limited to the exemplary embodiment shown.

Generally "one" may be understood as a single number or a plurality thereof, in particular within the meaning of "at least one" or "one or more", etc. provided this is not explicitly excluded, for example by the expression "just one", etc.

Moreover, numerical data may specifically encompass the specified number and a conventional tolerance range, provided this is not explicitly excluded.

The invention claimed is:

1. A method, comprising:
automatically starting a calibration process for calibrating an oxygen sensor of a household appliance in response to a status parameter of the household appliance reaching or exceeding a predetermined first threshold value;
wherein the status parameter comprises a door opening time.

2. The method of claim 1, wherein the household appliance is a steam cooking appliance.

3. The method of claim 1, wherein the oxygen sensor is a lambda probe.

4. The method of claim 3, further comprising:
measuring during the calibration process a pump flow of the lambda probe; and
when the pump flow remains for a predetermined time period within a predetermined fluctuation margin, selecting a value of the pump flow from the fluctuation margin as a reference value of the pump flow.

5. The method of claim 4, wherein an average value of the fluctuation margin is selected as the reference value of the pump flow.

6. The method of claim 1, wherein the calibration process is automatically started when a plurality of status parameters of the household appliance have reached predetermined-threshold values, respectively.

7. The method of claim 1, wherein the status parameter further comprises a time period elapsing since a last calibration, and the calibration process is automatically started in response to the time period reaching or exceeding a second threshold value, and the door opening time reaching or exceeding the first threshold value.

8. The method of claim 1, wherein the status parameter further comprises a cooking chamber temperature and the calibration process is automatically started in response to the cooking chamber temperature reaching or falling below a third threshold value, and the door opening time reaching or exceeding the first threshold value.

9. The method of claim 1, further comprising discontinuing the calibration process when the calibration process lasts longer than a predetermined threshold value.

10. The method of claim 1, further comprising discontinuing the calibration process when a cooking chamber door of the household appliance is closed.

11. The method of claim 1, further comprising:
storing a result of the calibration process; and
evaluating the result for a malfunction of the oxygen sensor.

12. The method of claim 11, further comprising:
measuring during the calibration process a pump flow of the lambda probe;
when the pump flow remains for a predetermined time period within a predetermined fluctuation margin, selecting a value of the pump flow from the fluctuation margin as a reference value of the pump flow; and
using the reference value of the pump flow as the result.

13. A household appliance, comprising:
a treatment chamber;
an oxygen sensor; and
a data processing device for determining a moisture content in the treatment chamber based on a measured value of the oxygen sensor, said household appliance being configured to automatically start a calibration process for calibrating the measured value of the oxygen sensor in response to a status parameter of the household appliance reaching or exceeding a predetermined first threshold value;

wherein the status parameter comprises a door opening time.

14. The household appliance of claim 13, wherein the household appliance is a steam cooking appliance, with the treatment chamber representing a cooking chamber configured for application of steam.

15. The household appliance of claim 14, wherein the status parameter further comprises a temperature in the cooking chamber, and the calibration process is automatically started in response to the temperature in the cooking chamber reaching or falling below a second threshold value, and the door opening time reaching or exceeding the first threshold value.

16. The household appliance of claim 13, wherein the oxygen sensor is a lambda probe.

17. The household appliance of claim 13, wherein the data processing device includes a memory device configured to store a result of the calibration process.

18. A method, comprising:

automatically starting a calibration process for calibrating an oxygen sensor of a household appliance in response to a status parameter of the household appliance reaching a predetermined threshold value, wherein the oxygen sensor is a lambda probe;

measuring, during the calibration process, a pump flow of the lambda probe; and in response to the pump flow remaining for a predetermined time period within a predetermined fluctuation margin, selecting a value of the pump flow from the fluctuation margin as a reference value of the pump flow.

19. The method of claim 18, further comprising:

storing the reference value of the pump flow as a result of the calibration process; and evaluating the result for a malfunction of the oxygen sensor.

* * * * *